United States Patent
Tauer et al.

(10) Patent No.: US 6,825,027 B2
(45) Date of Patent: Nov. 30, 2004

(54) METHOD OF PRODUCTION OF PURIFIED HEPATITIS A VIRUS PARTICLES AND VACCINE PREPARATION

(75) Inventors: Christa Tauer, Vienna (AT); Heidi Meyer, Vienna (AT); Artur Mitterer, Orth/Donau (AT); Noel Barrett, Klosterneuburg/Weidling (AT)

(73) Assignee: Baxter Healthcare S.A. (CH)

(*) Notice: Subject to any disclaimer, the term of this patent is extended or adjusted under 35 U.S.C. 154(b) by 0 days.

(21) Appl. No.: 10/006,205

(22) Filed: Dec. 10, 2001

(65) Prior Publication Data

US 2003/0124511 A1 Jul. 3, 2003

(51) Int. Cl.$^7$ .............................. C12Q 1/24; C12N 7/00; C12N 1/02; C12N 1/06; A61K 39/29
(52) U.S. Cl. ................... 435/239; 435/235.1; 435/800; 435/803; 435/814; 435/816; 435/962; 435/262; 435/325; 435/236; 435/238; 435/364; 435/380; 435/381; 424/226.1
(58) Field of Search .............................. 435/239, 235.1, 435/236, 238, 364, 380, 381, 816, 962, 262, 814, 325; 426/226.1

(56) References Cited

U.S. PATENT DOCUMENTS

| | | | |
|---|---|---|---|
| 4,783,407 A | 11/1988 | Provost et al. | |
| 5,268,292 A | 12/1993 | Robertson et al. | |
| 5,858,658 A | 1/1999 | Haemmerle et al. | |
| 6,100,061 A | 8/2000 | Reiter et al. | |

FOREIGN PATENT DOCUMENTS

| | | |
|---|---|---|
| EP | 0 339 667 B1 | 4/1989 |
| EP | 0 339 668 A2 | 4/1989 |
| EP | 0 583 142 A2 | 8/1993 |
| WO | WO 96/15231 | 5/1996 |
| WO | WO 00/23574 | 4/2000 |

OTHER PUBLICATIONS

MiKim–Breschkin et al. J. Virol. Methods 1991, vol. 32, pp. 121–124.*
Andre, et al., *Inactivated Candidate Vaccines for Hepatitis A*, Prog. Med. Virol., vol. 37, p. 72–95 (1990).
Armstrong, et al., *Development of the Formalin–Inactivated hepatitis A Vaccine, VAQTA™ from the Live Attenuated Virus Strain CR326F*, J. of Hepatology, vol. 18, p. 20–26 (1993).
Bader, *Hepatitis A Vaccine*, Amer. Journal of Gastroenterology, vol. 91:2, p. 217–222 (1996).
Binn, et al., *Primary Isolation and Serial Passage of Hepatits A Virus Strains in Primate Cell Cultures*, Journal of Clinical Microbiology, vol. 20:1, p. 28–33 (1984).
Binn, et al., *Preparation of a Prototype Inactivated Hepatitis A Virus Vaccine from Infected Cell Cultures*, Journal of Infectious Diseases, vol. 153:4, p. 749–756 (1986).
Bishop, et al., *Rapid and Efficient Purification of Hepatitis A Virus from Cell Culture*, Journal of Virological Methods, vol. 47, p. 203–216 (1994).
Bishop, et al., *Hepatitis A Virus Subviral Particles: Purification, Accumulation, and Relative Infectivity of Virions, Provirions and Procapsids*, Arch. Virol., vol. 142, p. 2147–2160 (1997).
Cinatl Jr., et al., *Protein–Free Culture of Vero Cells: A Substrate for Replication of Human Pathogenic Viruses*, Cell Biology International, vol. 17:9, p. 885–895 (1993).
Cohen, et al., *Hepatitis A Virus cDNA and Its RNA Transcripts Are Infectious in Cell Culture*, Journal of Virology, vol. 61:10, p. 3035–3040 (1987).
Dubois, et al., *Large–Scale Purification of Inactivated Hepatitis A Virus by Centrifugation in Non–Ionic Gradients*, Journal of Virological Methods, vol. 32, p. 327–334 (1991).
Flehmig, et al., *Immunogenicity of a Hepatitis A Virus Vaccine*, Journal of Medical Virology, vol. 22, p. 7–16 (1987).
Hagen, et al., *Use of a Nuclease Enzyme in the Purification of VAQTA®, a Hepatitis A Vaccine*, Biotechnology Appl. Biochem., vol. 23, p. 209–215 (1996).
Hennessey Jr., et al., *Evaluation of the Purity of a Purified, Inactivated Hepatitis A Vaccine (VAQTA™)*, Vaccine, vol. 17, p. 2830–2835 (1999).
Kessler, et al., *Suitability of MDCK Cells Grown in a Serum–Free Medium for Influenza Virus Production*, Dev. Biol. Stand., vol. 98, p. 13–21 (1999).
Kistner, et al., *Development of a Mammalian Cell (Vero) Derived Candidate influenza Virus Vaccine*, Vaccine, vol. 16: 9/10, p. 960–968 (1998).
Lemon, et al., *Antigenic Structure of Hepatitis A Virus, Molecular Aspects of Piocornavirus Infection and Detection*, p. 193–208 (1989).
Locamini, et al., *Restricted Replication of Human Hepatitis A Virus in Cell Culture: Intracellular Biochemical Studies*, Journal of Virology, vol. 37:1, p. 216–225 (1981).
Merten, et al., *Evaluation of the New Serum–Free Medium (MDSS2) for the Production of Different Biologicals:Use of Various Cell Lines*, Cytotechnology, vol. 14, p. 47–59 (1994).
Nasser et al., *Production of Cytopathology in FRhK–4 Cells by BS–C–1–Pasages Hepatitis A Virus*, Applied and Environmental Microbiology, vol. 53:12, p. 2967–2971 (1987).
Yokosawa, et al., *Affinity Chromatography of Trypsin and Related Enzymes*, Journal Biochem., vol. 79, p. 757–763 (1976).

* cited by examiner

Primary Examiner—James Housel
Assistant Examiner—Bao Qun Li
(74) Attorney, Agent, or Firm—Townsend and Townsend and Crew LLP (57) ABSTRACT

The present invention provides methods of purification of Hepatitis A Virus from the supernatant of an infected cell culture and production of a preparation of purified HAV antigen. The present invention is also directed to an HAV vaccine composition comprising a preparation consisting of purified mature HAV particles in an amount sufficient to induce a protective immune response in a mammal.

7 Claims, 3 Drawing Sheets

METHOD OF PRODUCTION OF PURIFIED HEPATITIS A VIRUS PARTICLES AND VACCINE PREPARATION

FIELD OF THE INVENTION

The present invention is directed to methods of purification of Hepatitis A Virus from the supernatant of an infected cell culture and production of a preparation of purified HAV antigen. The present invention is also directed to an HAV vaccine composition comprising a preparation consisting of purified mature HAV particles in an amount sufficient to induce a protective immune response in a mammal.

BACKGROUND OF THE INVENTION

Hepatitis A continues to cause sporadic cases, endemics and occasional deaths and is a public health problem all over the world. The infection is caused by Hepatitis A Virus (HAV) a member of the picornavirus family, a group of small non-enveloped RNA viruses. The virus particle is 27–32 nm in diameter and is composed of three polypeptides VP1, VP2 and VP3, cleaved from a single polypeptide precursor molecule.

Hepatitis A Virus (HAV) is the only hepatotropic virus which can be isolated from cell culture, but the virus is usually difficult to propagate, with long incubation period and no cytopathic effect. Even tough several primate cell types have been reported to support replication of HAV, such as fetal rhesus monkey kidney cell line (FRhk-4), primary African green monkey kidney cells (AGKM), continuous African green monkey kidney cells (BCS-1), these cannot generally be used for human vaccine because monkey kidneys often have high content of latent simian viruses which may become apparent in the course of virus production for vaccine. Other cell lines cannot be used because of the tumorogenic nature of some of these cells invokes constraints against their use for vaccine production. Mass production of primary human epithel, fibroblast or kidney cells or cell strains to propagate HAV is limited by the low passage number of these cells in culture. In fact, the applicable guidelines of the World Health organization (WHO) indicate that only a few cell lines are allowed for virus vaccine production.

One of the cell lines which is currently accepted and validated for the production of a vaccine applicable to humans are VERO cells. VERO cells are continuous monkey kidney cells that have been licensed for use in the manufacturing process of human vaccines and are currently used for the production of poliomyelitis and rabies vaccine. Attempts have also been made to use VERO cells for HAV production, but replication of HAV on VERO cells is limited because VERO cells have a temperature restriction of viral growth and virus is never found in the supernatant fluids of infected cells (Locarnini et al., 1981, J. Virol. 37: 216–225). U.S. Pat. No. 4,783,407 discloses the production of HAV on VERO cells in roller bottles at a temperature no higher than 33° C. to overcome the temperature restriction. In this system about 50 $\mu$g HAV antigen can be obtained per roller bottle followed by freeze-thawing of the cultured cells. A commercial vaccine based on propagation of HAV on VERO cells has never been described.

So far, formalin inactivated HAV vaccines have been produced for clinical trials (Andre et al., 1990, In: Melnick (ed): Prog. Med. Virol. Basel, Karger 37: 72–95, Armstrong et al, 1993, J. Hepatology 18:20–26) and four have been licensed, which induce long-lasting immunity and protection from primary infection. The manufacturing process of the currently available inactivated HAV whole virus vaccines uses the human embryonic lung fibroblast cell line MRC-5 as host cells which grow slowly in tissue culture and only by addition of fetal calf serum.

The problems arising from the use of serum in the cell culture and/or protein additives derived from an animal or human source added to the culture medium, i.e. the varying quality and composition of different batches and the risk of contamination with mycoplasma, viruses or BSE-agent, are well-known. Therefore, many attempts are being made to provide efficient host systems and cultivation conditions that do not require serum or other serum derived compounds. Besides, avoidance of contamination by the use of serum free medium would allow more efficient purification due to less contamination in the starting material comprising the viral antigen.

Binn et al. (1984. J. Clincal. Microbiol. 20: 28–33) tested several primate cell types for replication of HAV and optimal conditions for isolation and production of quantities of virus. Serum free production of HAV on BSC-1 cells, a heterodiploid cell line that until now has not been used for preparation of vaccines for use in humans, in roller flasks revealed that after 21 days of the cultivation process virus antigen can be found in the supernatant and the cell fraction. Cells maintained in serum free medium supported viral growth equal to those maintained in serum. A candidate HAV vaccine obtained by low speed centrifugation of supernatant of freeze-thawed cells and supernatant fluid of infected BSC-1 cells maintained in serum free medium was described by Binn et al., 1986 (J. Infect. Diseases 153: 749–756).

Flehmig et al. (1987. J. Medical Virol. 22:7–16) prepared candidate HAV vaccine with HAV isolated from cell culture supernatant of persistently infected normal human embryonic fibroblasts grown in serum containing medium which had shown no cytopathic effect. Thereby, HAV antigen isolated and purified in serial steps from large amounts of supernatants produced in NUNC cell factories was used for vaccination tests.

However, all strains of HAV which have been grown in cell culture are characterized by inefficient release of virus into the culture supernatant. Although as much as 50% of infectious virus may be released, typically less than 30% of infectious virus is extracellular (Nasser et al., 1987. Appl. Environmental Microbiol. 53: 2967–2971). Therefore, antigen is often undetectable in unconcentrated culture supernatant and the concentrations of large volumes contributes to difficulties in HAV purification with this process. Because HAV antigen is not efficiently released into the culture supernatant and methods to concentrate the large volume are costly (Bishop et al., 1994. J. Virol. Meth. 47:203–216), most purification processes described uses HAV antigen from cell lysate of intracellularly produced virus as source for production of HAV vaccine (EP 0 339 667; EP 0 583 142, Andre et al., 1990, In: Melnick (ed): Prog. Med. Virol. Basel, Karger 37: 72–95; Armstrong et al, 1993, J. Hepatology 18:20–26); Hagen et al., 1996, Biotechnol. Appl. Biochem. 23:209–215; Bader et al., 1996, Amer. J. Gastroenterol. 91:217–222, Hennessey et al., 1999, Vaccine 17:2830–2885, WO 00/23574). However, these processes are time-consuming, make use of detergent necessary to release intracellularly produced antigen from the cells and need intense and serial purification steps to remove detergent and contaminants derived from the cells.

For the induction of a protective immune response it is suggested that the capsid proteins must be folded and assembled in the right confirmation and that the precursor proteins are not capable to elicit a protective immune response. Mature HAV particles consist of three virus capsid proteins (VP1, VP2, VP3). These proteins are derived from a single precursor molecule (P1) by several sequential cleavages. During virus maturation and assembly different intermediates are formed. The pre-cleaved proteins assemble first to a pentameric structure and then 60 pentamers form a provirion. The provirions consist of VP1, VP0 and VP3. The mature virus particles derive from these provirions after a last maturation cleavage of VP0 in VP2 and VP4. VP4 is not present in the mature virus particle.

HAV large scale preparations from the cell lysates and/or the cell culture supernatants contain mixed populations of mature virions, provirions and procapsids (Bishop et al., 1997. Arch. Virol. 142:2147–2160; EP 339 667, EP 339 668). The mature virus is composed of polypeptides VP1, VP2 and VP3, wherein the capsid proteins VP1 and VP3 contain the major antigenic sites and are capable to induce neutralizing antibodies (Lemon et al., 1989, In: Semler et al. eds. Molecular aspects of picornavirus and detection. Washington, D.C.: ASM p 193–208). Attempts have been made to purify HAV and separate the different forms of HAV particles. Bishop et al. 1997 (supra) used linear gradient centrifugation to separate the different HAV particle forms and found that HAV particles at a density of 1.32–1.33 g/cm$^3$ are a mixture of VP0- and VP2-containing particles indicating an incomplete separation of provirions and mature virions. In the fractions containing predominantly mature HAV virions more VP2 than VP0 in a ration of 55% to 45%, respectively, are found. Both virions and provirions are detected in cell lysates and culture supernatant and, in addition to VP0, released particles containing variable levels of VP1 precursor protein PX, having a molecular weight of about 67 KD, was detected. Dubois et al. (1991. J. Virol. Meth. 32:327–334) prepared a vaccine from a major peak fraction at a density of 1.33 g/cm$^3$ comprising complete particles purified by isopycnic centrifugation. U.S. Pat. No. 5,268,292 described isolation and purification of HAV from persistently infected cells, and found that most of silver stained protein is accounted for by the viral polypeptides VP1, VP2 and VP3, but also a polypeptide of about 67 kD was detectable.

The worldwide market demand for HAV vaccines is on the order of 100 Million doses per year. Efficient vaccine production requires the growth of large-scale quantities of virus produced in high yields from a host system. Moreover, there is a need for an approach to viral propagation, employing materials that are already available and requiring a minimal number of time-consuming manipulations, wherein the selection of a combination of host cells, culture medium, growth conditions and production system is essential to achieve an efficient production process. Most vaccines have not been purified to preserve sensitive biological activity which is critical to the efficacy of the vaccine. A pure product would be expected to produce more a consistent vaccine having higher immunogenicity and produce fewer side effects from a clinical point of view.

BRIEF SUMMARY OF THE INVENTION

It is an object of the present invention to provide a method of purification of HAV from cell culture supernatant of an infected cell culture.

It is another object of the invention to provide for a method of isolation of complete HAV particles from the supernatant of an infected cell culture.

It is another object of the invention to provide for a method of isolation of mature HAV particles from the supernatant of an infected cell culture.

It is another object of the present invention to provide a method for production of purified preparation of HAV particles.

It is also an object of the invention to provide a method for production of a purified preparation consisting of complete HAV particles It is also an object of the invention to provide for a method for production of a purified preparation consisting of mature HAV particles.

It is an object of the present invention to provide a method for production of preparation consisting of inactivated, purified mature HAV particles.

It is also an object of the invention to provide a preparation consisting of purified HAV particles.

It is another object of the invention to provide a vaccine purified complete HAV antigen.

It is another object of the invention to provide a vaccine purified mature HAV antigen.

BRIEF DESCRIPTION OF THE DRAWINGS

FIG. 1B shows Western blot analysis of different intermediates of the HAV purification process using HAV specific guinea pig sera. It is shown in lane 1: HAV Concentrate (starting material), lane 2: open, lane 3: filtrate of ultrafiltration step 10-fold concentrate; lane 4: retentate of ultrafiltration step 10-fold concentrate; lane 5: open, lane 6: diafiltrate 1 of diafiltration step 1; lane 7: diaretentate 1 of diafiltration step 1; lane 8: diaretentate 1 after filtration with 0.22μ filter; lane 9: open, lane 10: diaretentate plus Benzonase® (after 3 hours of treatment); lane 11: diaretentate plus protease (after 24 hours of treatment); lane 12: open; lane 13: diafiltrate 2 of diafiltration with buffer; lane 14: diaretentate 2; lane 15: open; lane 16: diaretentate 2 (using 0.22μ filter); lane 17: open and lane 18: molecular weight standard.

DETAILED DESCRIPTION OF THE INVENTION

In the present invention a process has been established that allows for the production of HAV antigen under serum-free conditions and the simple purification of HAV antigen from the cell culture supernatant of infected cells. Contaminating impurities which might derive from the cells or the cell culture medium are efficiently removed by the method of the invention.

In accordance with one object of the invention there is provided a simple method for purification of HAV antigen that yields a high degree of purity within single purification step. By the method, HAV antigen is purified from the cell culture supernatant of an HAV infected cell culture by concentrating the cell culture supernatant comprising the HAV produced and released into the culture medium by filtering, treating the concentrated HAV preparation with a nucleic acid degrading agent and a protease, filtering the preparation treated with said agent and protease, and isolating a preparation of complete purified HAV particles.

The purified HAV preparation of complete HAV particles is then subjected to a further step of isolating purified mature HAV particles from the purified HAV preparation of complete HAV particles. The method of the invention comprising a purification and an isolation step results in a purified HAV preparation suitable for human clinical use, the preparation being substantially free of contaminants from the cells and the cell culture.

The term "complete HAV particle" means RNA-containing HAV particle of mature, infectious HAV virion particle which consists of capsid proteins VP1, VP2 and VP3, and immature provirions which contain VP1, VP3 and VP0 precursor polypeptide.

The term "mature HAV particle" means RNA-containing HAV virion particle which consists of capsid proteins VP1, VP2 and VP3 only.

The term "suitable for human clinical use" means that the endotoxin content of 10 µg antigen is less than about 2 IU, as determined by the chromogenic LAL test. In addition, the level of contaminating DNA, particularly of VERO cells DNA, as determined by quantitative PCR using internal standard, is, according to the invention less, than about 100 pg per 100 IU HAV antigen, preferably less than about 50 pg, more preferably less than about 40 pg. A vaccine dose having about 20 IU HAV antigen therefore has less than about 20 pg, preferably less than about 10, most preferably less than about 8 pg contaminating DNA. Furthermore, the level of cellular contaminants as determined by SDS-PAGE and Western-blot analysis per dose of virus antigen is less than about 0.1% of the total protein content, preferably less than about 0.05%.

The term "substantially free" means that the amount of contaminating impurities such as proteins derived from the cells or the cell culture or contaminating cellular nucleic, is below the detection limit of a most sensitive state of the art detection method. Western blot analysis and densitimetric methods are used to test the amount of contaminating proteins in a sample. The highly sensitive PCR method as described in U.S. Pat. No. 5,858,658 for nucleic acid quantification, particular for genomic VERO cell DNA, can be used to quantify the residual amount of nucleic acid in a sample.

The term "contaminants from the cells and the cell culture medium" means cell fragments, cellular polypeptides and proteins, cellular nucleic acids and other cell derived macromolecules as well as polypeptides and proteins from the medium.

The term "cellular nucleic acids" means heterogeneous DNA or RNA derived from the cells that have been infected with the virus used to propagate the virus.

The purified HAV antigen of the present invention is substantially free of contaminating proteins and nucleic acid, suitable for human clinical use and is stable. By "purified Hepatitis A Virus antigen" is meant a purity as determined by SDS-PAGE (silver stained or commassie stained) and Western blot and a ration of HAV antigen to total protein amount, said purity is preferably greater than about 98%.

In accordance with the objects of the invention, there is provided a method of production of a purified preparation of complete HAV particle comprising the steps of treating an HAV preparation derived from the cell culture supernatant of an HAV infected cell culture with a nucleic acid degrading agent and a protease, and isolating a preparation of complete HAV particles. The HAV containing supernatant can be harvested and concentrated prior the treatment with the nucleic acid degrading agent and the protease. The HAV containing cell culture supernatant can be from any cell culture that produces and releases HAV into the supernatant. The cell culture is preferably a serum-free cell culture.

According to one embodiment of the method, the cell culture supernatant provided is from HAV infected VERO cells. The VERO cells can be in suspension, roller bottles or flasks. According to preferred embodiment, the VERO cells are preferably a microcarrier culture wherein the cells are bound to the microcarrier. The microcarrier can be a microcarrier selected from the group of microcarriers based on dextran, collagen, plastic, gelatine and cellulose and others as described in Butler (1988. In: Spier & Griffiths, Animal cell Biotechnology 3:283–303). The cells are preferably grown the serum-free or serum and protein free medium. The serum free or serum and protein free medium can be one as described for example by Kistner et al. (1998. Vaccine 16: 960–968), Merten et al. (1994. Cytotech. 14:47–59), Cinatl. et al. (1993. Cell Biology Internat. 17:885–895), Kessler et al. (1999. Dev. Biol. Stand. 98:13–21), WO 96/15231, U.S. Pat. No. 6,100,061 or any other serum free or serum and protein free medium known in the art. The cells are preferably grown from the ampoule to the biomass in serum free or serum and protein free medium and kept under the respective culture medium conditions during cell culture growth, virus propagation and virus production process.

However, the method of the invention can be applied to any cell culture supernatant of HAV-infected cells that are known to release HAV particles into the cell culture medium as described for example by Binns et al. (1984. supra) or Flehmig et al. (1987. supra), whereby any host cell can be used that is susceptible to HAV and releases HAV into the medium.

Due to the dilution of HAV particles in the cell culture medium of HAV infected cells, the HAV antigen in the medium is concentrated by reduction of medium volume. This can be done by any method known to reduce liquid volume and concentrate a virus-containing liquid, such as centrifugation, filtering, precipitation, 2-phase partitioning. According to a preferred aspect of the invention the HAV-containing medium harvest is concentrated by filtering. According to present method an ultrafilter is preferred. This has the additional advantage that contaminants having a smaller size than HAV particles can be removed in the same step. The obtained concentrate comprising HAV is then treated with a nucleic acid degrading agent and a protease. The agent and protease might need a specific conditions, such as ionic strength, pH and buffer, for their activity. To provide efficient buffer condition for activity, the cell medium might be removed and exchanged by a buffer which allows efficient activity of the nucleic acid degrading agent and protease in the HAV comprising preparation. This can be done by methods known in the art, such as dialysis and buffer exchange by ultrafiltration or chromatography. According to a preferred aspect of the method of the invention this is done by filtering. This filtering is preferably done by diafiltration.

The nucleic acid degrading agent according to the invention can be an enzyme which degrades nucleic acid, preferably a nucleic acid degradation enzyme, such as a nuclease, a DNase, a RNA or endonuclease, such as from Serratia marcescens, commercial available as Benzonase® (Benzon PharmaA/S).

The protease used for degradation of high molecular weight proteins and polypeptide can be any protease known in the art, such as for example proteinase K, trypsin, chymotrypsin. However, proteases derived from an animal source, such as bovine or porcine trypsin, bear the risk to be contaminated with infecting agents, like BSE.

Therefore, according to a preferred aspect of the method of the invention, the HAV-containing preparation is treated with protease of microbial origin. The microbial protease can be Pronase. Pronase is a mixture of different enzymes from *Streptomyces griseus* (S.g.) and is commercially available. This cocktail contains many different proteins including proteases, phosphatases, collagenases and a trypsin-like protease, commonly called S.g. trypsin (SGT). This enzyme shows a large extent of similarity to animal-derived trypsin with respect to its selectivity and activity. Because pronase is a composition of different enzymes, one of the enzyme activities might have an adverse effect on HAV in the preparation.

According to a preferred embodiment a purified trypsin-like enzyme of a microbial protease is used. In particular, the trypsin-like enzyme *Streptomyces griseus* trypsin (SGT), a purified fraction of Pronase, is used. The purified SGT is preferably obtained by a method of affinity chromatography on benzamidine and elution of purified SGT with an eluting agent comprising 0.5 to 1.2 M arginine. It has been found that the SGT purified by this method is very efficient and can be used with reduced protein load to the medium due to its high specific activity. SGT purified from Pronase by other methods known in the art can be used in the method of the invention as well. Such methods included such as described by Yokosawa et al. (1976. J. Biochem. 79:757–763) or other chromatography methods.

After treatment of the HAV preparation with the nucleic acid degrading agent and protease, the agent and protease, as well as the degradation products resulting from their activity, such as low molecular weight fragments of high molecular weight macromolecules, such as nucleic acids or proteins, and other impurities are removed from the preparation. According to the method of the invention, the removal of impurities is performed by filtering. Thereby, a purified preparation having less than 30 pg contaminating nucleic acid/IU HAV antigen is obtained. The preparation has at least 5000 IU of HAV antigen/mg protein.

It has been found that by filtering impurities are efficiently removed and complete HAV particles are isolated within one single step. The purified preparation of complete HAV particle obtained as described above, therefore, consists essentially of complete HAV particles, wherein complete HAV particles are purified from a cell culture supernatant of HAV infected cells by filtering.

The purified preparation of complete HAV particle as obtained by the method described above can be used as source for isolating of mature HAV particle and for the production of a purified HAV preparation of mature HAV particles. The different HAV particle forms (virion and provirion) in the preparation can separated by conventional centrifugation, such as isopycnic centrifugation on sucrose gradient, CsCl-gradient or gel chromatography or preparative Field Flow Fractionation.

In accordance with another object of the invention, there is provided a method of production of a purified preparation of mature HAV particles. The method comprises the steps of providing a cell culture supernatant of an HAV infected cell culture, treating the HAV preparation with a nucleic acid degrading agent and a protease, isolating a preparation of complete HAV particles and isolating purified mature HAV virions from said preparation of complete HAV particles. The mature HAV virions can be isolated by centrifugation, such as isopycnic centrifugation. The centrifugation is preferably a isopycnic centrifugation with a sucrose-gradient, pelleting or centrifugation with a sucrose cushion. The method, therefore provides for production of a purified HAV preparation of mature HAV particles, wherein the mature HAV particles are isolated from a preparation of complete HAV particles. The preparation of mature HAV particles is obtained from a cell culture supernatant of HAV infected cells by filtering and isopycnic centrifugation. The method described is simple, efficient and cost-reducing and provides for a pure product which has not been described in the prior art.

By combining specific conditions starting from a cell culture which is grown in serum free or serum and protein free medium, using the cell-free supernatant of HAV infected serum-free or serum-and protein-free cell culture as source for production of purified HAV, the main sources of possible contamination deriving from the cells and the cell culture medium are avoided. However, it could not have been expected that cells bound to microcarriers release virus produced into the cell culture medium from which HAV particles can be efficiently purified by the method of the invention. The purification by filtering makes the method easy to adapt to large scale purification scheme. The additional treatment with a nucleic acid degrading agent and a protease destroys all high molecular weight macromolecules which then can be removed also by filtering.

The purified HAV preparation of the invention is free of contaminating proteins from the cells or the cell culture medium. This is determined by Western blot analysis with specific antibodies against the host cell proteins and determination of the ratio of HAV antigen to total protein amount in the preparation. The efficiency of removal of contamination nucleic acid derived from the cells is determined by a highly sensitive method of quantification of the residual nucleic acid as described in U.S. Pat. No. 5,858,658. Other quantitative nucleic acid analysis methods known in the art can be used as well. The purified HAV preparation of the method of the invention has less than about 0.5 pg contaminating nucleic acid/IU HAV antigen.

Attenuated HAV is known in the art and reduces the risk of transmission of infectious particles. However, inactivation of vaccine viruses, even attenuated, for use in a human vaccine increases the safety of the vaccine. According to one embodiment of the method, the method comprises a step of treating the purified HAV particles with a virus inactivating agent. The inactivating agent can be any agent known in the art with inactivating activity, such as formalin, BEI, laser light, UV light, chemical treatment such as methylene blue, psoralen or a combination of any thereof. Preferably, the virus is inactivated with formalin. The virus inactivation can be done at any stage during purification process, however, most conveniently the treatment with the virus inactivation agent is prior to the final purification step, whereby mature HAV particles are isolated from the preparation of complete HAV particle forms.

According to this aspect of the invention, the method provides for production of a purified, inactivated HAV preparation of complete HAV particles, wherein complete HAV particles are purified from a cell culture supernatant of HAV infected cells by filtering and virus inactivation treatment.

According to another aspect of the invention, the method provides for production of a purified, inactivated HAV preparation of mature HAV particles, wherein mature HAV particles are purified from a cell culture supernatant of HAV infected cells by filtering and centrifugation. The HAV particles can be inactivated prior or after centrifugation and isolation of mature HAV particles, whereby the inactivation treatment prior centrifugation is preferred. This allows the removal of the contaminating residues of the inactivating agent by the final purification and isolation step.

According to another aspect, the invention provides for a method of isolating complete HAV particles virions from a cell culture supernatant of HAV infected cells. This method comprises the steps of filtering a cell-free cell culture supernatant HAV harvest, treating the filtered HAV preparation with a nucleic acid degrading agent and a protease, and isolating complete HAV particles. The isolated complete HAV particles are free of any HAV precursor polypeptide, such as P1 or PX. The method does not comprise any other purification and isolation step, except filtering.

By the method described above, a purified preparation of HAV is provided which consists of purified complete HAV particles being substantially free from HAV precursor polypeptide P1 and from contaminating protein from the cell or the cell culture. The preparation has less than 30 pg contaminating nucleic acid/IU HAV antigen, and has at least 5000 IU of HAV antigen/mg protein.

According to another aspect, the invention provides for a method of isolating mature HAV particles from a cell culture supernatant of HAV infected cells. The method comprises the steps of treating the filtered HAV preparation derived from the cell culture supernatant of an HAV-infected cell culture with a nucleic acid degrading agent and a protease, isolating complete HAV particles and further isolating mature HAV virion particles. The cell-free culture supernatant HAV is filtered prior to treatment with the nucleic acid degrading agent and protease. The isolation of mature HAV particles is preferably performed by centrifugation. The method does not comprise any other purification or isolation methods, such as chromatography steps.

By the method described above, a purified preparation of mature HAV particles that is free from contaminating protein from the cell or the cell culture is provided. The purified mature HAV virion particles are free from HAV precursor polypeptide P1 and free from HAV provirions. The preparation has less than 0,5 pg contaminating nucleic acid from the cells or the cell culture/IU of HAV antigen and has at least 5000 IU of HAV antigen/mg protein.

The preparation can further comprise a physiologically acceptable carrier and/or stabilizer.

The preparation can be formulated as immunogenic composition. According to one embodiment of the invention the immunogenic composition is an aqueous solution of HAV particles and can be used directly.

The purified HAV particles can be mixed or adsorbed with any of the various known adjuvant. Such adjuvants include, but are not limited to, aluminium hydroxide, aluminium phosphate, saponins, such as Quil A, monophosphoryl lipid A (MPL) and 3-deacylated monophosphoryl lipid A (3D-MPL), or QS21.

According to one aspect of the invention, there is provided a method for production of HAV vaccine comprising the steps of treating the HAV preparation of a supernatant of an HAV infected cell culture with a nucleic acid degrading agent and a protease, isolating a preparation of complete HAV particles and formulate the purified complete HAV particles in an immunogenic composition.

According to another aspect of the invention, there is provided a method for production of HAV vaccine comprising the steps of treating the HAV preparation of a supernatant of an HAV-infected cell culture with a nucleic acid degrading agent and a protease, isolating a preparation of complete HAV particles, isolating purified mature HAV virions from said preparation of complete HAV particles, and preparing an immunogenic composition comprising a preparation of purified, mature HAV virions The vaccine can comprise purified HAV particles that have been treated with a virus inactivating agent. According to an additional aspect of the invention, there is provided a method for production of an HAV vaccine comprising inactivated HAV particles, either purified complete HAV particles or mature HAV virion particles. The method therefore comprises the step of treating the purified preparation of complete HAV with an inactivating agent. The inactivated agent is then removed from the HAV preparation by conventional methods. The agent can also be removed by filtering and isolation of inactivated mature HAV particles as described above. In the final step an immunogenic composition comprising a preparation of purified, inactivated complete or mature HAV virions is prepared.

In accordance with another aspect of the invention there is provided an HAV vaccine comprising a host protective amount of a preparation of purified mature HAV particle being free from contaminations from the cell or the cell culture. The preparation used to formulate the vaccine is free of HAV precursor polypeptide P1 and HAV provirions.

The term "host protective amount" means the critical protective dose of viral antigen in the vaccine, wherein said amount is effective to immunize a susceptible mammal against Hepatitis A Virus infection and induces a protective immune response in the host.

The preparations of mature HAV particles of the invention have a higher immunogenicity in the animal models tested than known, commercial available HAV preparations. The antigen dose (IU) in the vaccine preparation of the present invention needed to obtain an efficient immune response is lower than other vaccine preparations. This can be explained, at least in part, by the higher purity of the preparations of the invention. In addition, the preparations consist of mature HAV particles which consist of HAV capsid proteins VP1, VP2 and VP3 only, which contain the major antigenic sites for induction of neutralizing antibodies. The preparations do not comprise immature particles, provirions or HAV precursor polypeptide which would reduce the ratio of immunogenic sites in the HAV preparation.

The vaccine composition of the invention, therefore, preferably comprises an host protective amount of HAV antigen of less than about 25 IU of HAV antigen/dose, preferably less than about 20 IU of HAV antigen/dose. According to a preferred embodiment of the invention the host protective amount in the vaccine is between about 5 and about 25 IU of HAV antigen/dose. However, higher concentration can be used. The amount of contaminating nucleic acid from the cell in the vaccine composition is less than about 0.5 pg/IU antigen. The vaccine composition is stable, meaning that the mature HAV particles in the composition do not appreciably degrade, i.e. after one year stored at 2–8° C., more than 95% of HAV antigen remains as particle structure as determined by antigen ELISA and efficacy studies in animals compared to a standard reference.

The immunogenic composition consisting of purified mature HAV particles can further comprise a buffer and/or a physiologically acceptable carrier. The composition can comprise an adjuvant. It also is shown that a composition comprising low concentrations of an adjuvant induces higher antibody and neutralizing antibody titers than one comprising a higher adjuvant concentration (see Example 5). Therefore, the vaccine composition can comprise small amounts of adjuvant. The final concentration of the adjuvant in the vaccine can be between about 0.001% and about 0.5% (w/v), preferably between about 0.05 and about 0.1% (w/v). The adjuvant can be the standard adjuvant, aluminum hydroxide or aluminum phosphate. The immunogenic HAV preparation can comprise other ingredients such as an immune stimulating agent.

According to another aspect, the vaccine further comprises at least a second antigen from a pathogen. The antigen can be from a virus or a bacteria pathogenic to humans.

According to one embodiment, the vaccine further comprises Hepatitis B virus antigen. Preferably, the HBV antigen is the HBV surface antigen (HBsAg), wherein the HBV surface antigen is selected from the group of HBV preS1-preS2-S (large antigen), preS2-S antigen (middle antigen) or S-antigen (small antigen) or a mixture thereof. HBsAg can be mixed with the purified HAV particles to obtain an HAV/HBV vaccine composition. The HBV antigen can be combined with an immune stimulating agent, or an adjuvant such as aluminum salt or any other adjuvant as described above.

According to another aspect, the vaccine may further comprise an antigen derived from a pathogen selected from the group of H. influenzae, Meningococcus A, B, C, W or Y, Streptococcus pneumoniae, Pneumococcus.

The advantages of the present invention are illustrated in the following examples. The examples are illustrative of the invention but do not limit its scope.

EXAMPLE 1

Production of HAV Antigen on VERO Cells

Full length cDNA from the genome of attenuated strain HM175/7 cloned in the bacterial plasmid pHAV/7 (Cohen et al., 1987, J. Virol. 61:3035–3039) is used to prepare full length genomic RNA by in vitro transcription. Serum free VERO cells at 34° C. are transfected with in vitro transcribed HAV RNA to generate virus stocks of HAV HM175/7 free of adventitious agents.

VERO cells (African Green Monkey, Cercopthecus aethiops, kidney) are used as production cell line. The cells have been obtained from the American Type Cell Culture Collection, Rockville, Md. at a passage number 124 under the designation ATCC CCL 81. The cells are adapted to grow in serum or serum and protein free medium as described in Kistner et al., 1998 (supra) or WO 96/15231. For growth in serum free medium, a basal DMEM HAM's F12 medium supplemented with inorganic salts, amino acids, sodium bicarbonate and yeast or soy bean extract is used. The working cell bank is prepared without the use of any animal derived medium components.

One ampoule of a working cells bank (WCB) of VERO cells cultivated in DMEM medium mixed with Ham's F12 nutrient mixture in a ratio 1:1 is resuspended in medium containing serum and in serum free medium supplemented either with soy bean or yeast extract. Subcultivation is performed by using purified Streptomyces griseus trypsin (1 µg/ml) to avoid any agent derived from an animal source which could comprise any pathogenic causing agent. After subcultivation in Roux and roller bottles, $6-8 \times 10^7$ cells/ gram microcarrier (Cytodex III®,Pharmacia) are inoculated in a 12 l stirred tank fermenter. The cells are grown at 37° C. for 6–8 days. The culture conditions of oxygen saturation 20%+/−10% and pH 7.1 +/−0.2 and stirring speed of 30 –60 rpm are controlled. On the second day after inoculation at a cell density of $6 \times 10^5$ to $1 \times 10^6$ cells/ml a virus suspension of HAV HM175/7 with a multiplicity of infection (m.o.i.) between 0.1 and 1.0 is pumped into the fermenter at a temperature of 34° C. After two hours to allow for virus adsorption, medium perfusion is started. Half of the fermenter volume is exchanged against fresh medium every day. The microcarrier and the attached cells are retained in the fermenter by a sieve. During the fermentation process pH 7.1, $O_2$ (30%), stirring speed 30–60 rpm) and temperature of 34° C. is controlled.

For large scale production of HAV HM175/7 virus, a VERO cell culture at biomass of $1 \times 10^{11}$ is seeded on a microcarrier and propagated at 37° C. under serum free medium conditions in a 100 l fermenter. The temperature is lowered to 34° C. and during the following fermentation cycles the cell number increases 8 to 10 fold. In the final fermenter the cells are infected with HAV at a m.o.i. of 0.01 to 1.0. Propagation of the infected cells at 34° C. up to 350 days can be performed with permanent perfusion of the cell culture medium. When virus antigen is detected in the medium, the virus containing supernatant is collected and stored at 4° C. The harvest of the cell culture supernatant is started at days 35–45 after infection.

EXAMPLE 2

Purification of Virus Harvest

The virus harvest of cell culture supernatant of Example 1 is concentrated 100 times by ultrafiltration on a Prostak Ultrafilter 200 K followed by a diafiltration step (Prostak 200 K, Diafilter) with a buffer exchanged to 50 mM Tris buffer pH 8.0, 0.01% Tween. Residual host cell nucleic acid that may be present in the preparation is removed by incubation of the Diaretenate with Benzonase® (Sigma) 1000 U/l (in 1 mM $MgCl_2$) for 3 hours at room temperature. Subsequently, purified trypsin-like microbial protease of Streptomyces griseus (SGT) at a concentration of 0.5 to 5 U/ml is added and the retentate is further incubated for 24 hours at room temperature. The host cell contaminants, i.e. nucleic acids and/or proteins, are removed by diafiltration on a 100K membrane with a 20 mM PBS pH 7.4 as buffer.

EXAMPLE 3
Efficacy of Initial Purification of HAV

The efficacy of the first purification step is investigated with two cell culture harvests at different time intervals during the continuous fermentation process. The purification is performed as described in Example 2 and samples are drawn from the starting material, after concentration by ultra/diafiltration and after enzyme treatment followed by final diafiltration step.

A. Western Blot Analysis

Samples containing at least 1000 ELISA units/ml of HAV antigen are taken during each filtering step, subjected to SDS-PAGE, and Silver stained to visualize total protein or analyzed by Western blot analysis to determine HAV specific antigens.

Figure 1:
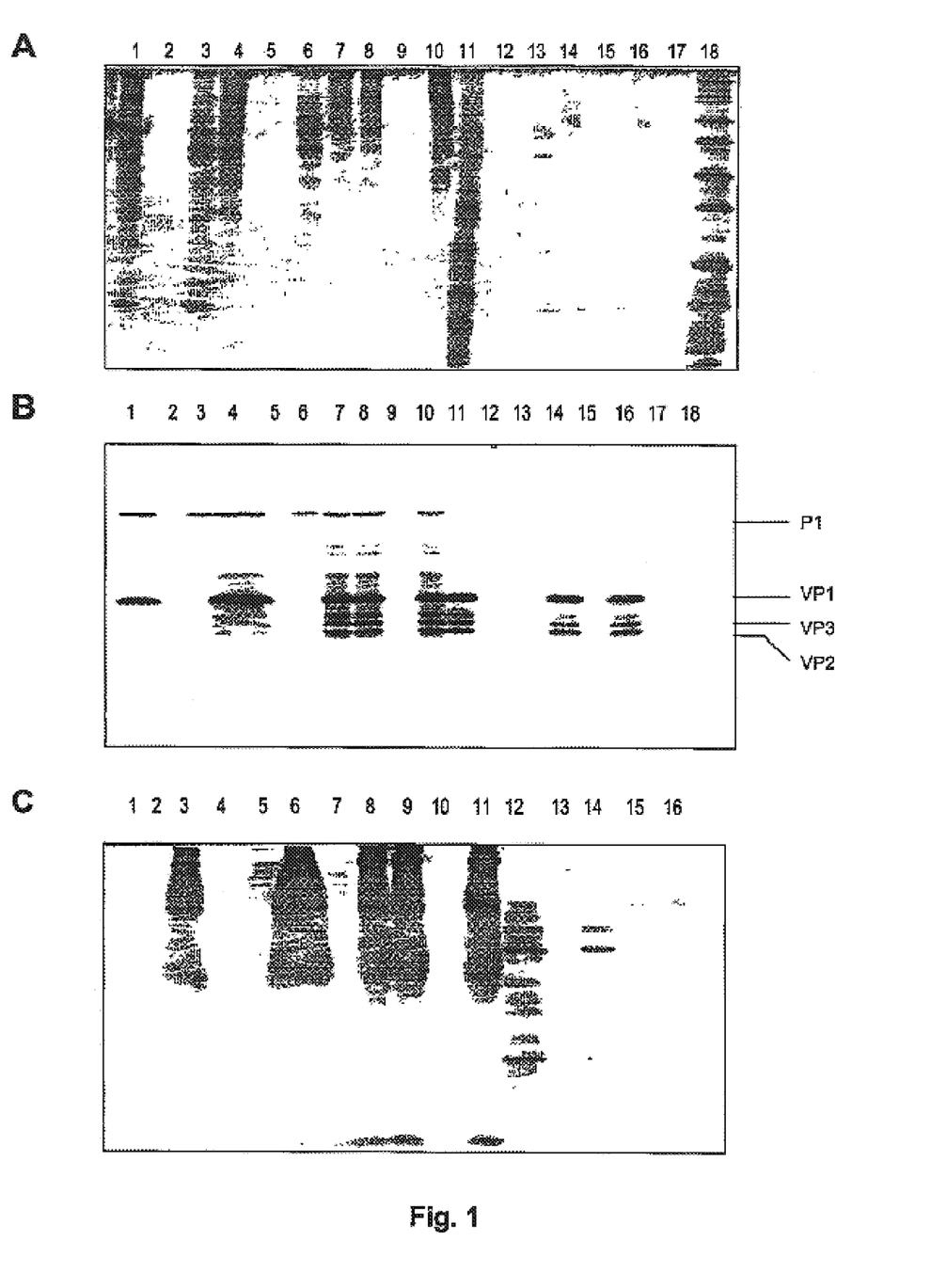
FIG. 1A shows the SDS-PAGE protein pattern and silver staining of the different intermediates of the HAV purification process.
FIG. 1C shows a Western blot analysis of the different intermediates of the HAV purification process using VERO cell specific antiserum. Lane 1: molecular weight standard; lane 2: open; lane 3: HAV Concentrate (starting material), lane 4: open, lane 5: filtrate of ultrafiltration step 10-fold concentrate; lane 6: retentate of ultrafiltration step 10-fold concentrate; lane 7: diafiltrate 1 of diafiltration step 1; lane 8: diaretentate 1 of diafiltration step 1; lane 9: diaretentate 1 after filtration with 0.22μ filter; lane 10: open, lane 11: diaretentate plus Benzonase® (after 3 hours of treatment); lane 12: diaretentate plus protease (after 24 hours of treatment); lane 13: open; lane 14: diafiltrate 2 of diafiltration with buffer; lane 15: diaretentate 2; lane 16: diaretentate 2 (using 0.22μ filter).

FIG. 1A shows the protein pattern of the various intermediates after silver staining. A broad range of polypeptides could be detected in the starting material and first intermediates of the purification procedure (FIG. 1A lanes 1–11), whereas only one slight protein band was left after protease treatment and diafiltration (FIG. 1A, lane 14 and 16). HAV specific capsid proteins are not detectable by silver staining neither in the starting material nor in the purified diaretentate.

HAV specific antigens are identified by Western blot analysis using an antiserum specific for HAV capsid proteins (FIG. 1B). It can be seen that HAV precursor protein (P1) is removed during the purification process (FIG. 1B, lane 1–11). In the starting material of cell culture supernatant HAV specific polypeptides are detected that are not present in the diaretentate after protease treatment, whereas the HAV specific capsid proteins VP1, VP2 and VP3 are not effected by protease treatment (FIG. 1B, lane 14 and 16). The analysis of different intermediates by silver staining and Western blot clearly demonstrated the efficacy of the purification procedure.

Western blot analysis using an antiserum raised against VERO cell proteins (FIG. 1C) reveals that in the starting material and purification intermediates a broad range of predominantly high molecular weight VERO proteins are detectable. In the final retentate only a minor VERO cell contaminants are detectable (FIG. 1C, lane 15–16).

The primary purification procedure using solely serial filtering steps is found to be highly effective in removing host cell contaminants as well as viral precursor proteins. High molecular weight VERO cell proteins are fragmented by protease treatment and afterwards efficiently removed by a diafiltration step. Furthermore, the purification procedure lead to a pure preparation of infectious HAV particles. Infectious HAV particles consist of three virus capsid proteins (VP1, VP2, VP3). These proteins are derived from a single polypeptide precursor molecule (P1) through several sequential cleavages during the virus maturation and assembly process. For the induction of a protective immune response, it is suggested that the capsid proteins must be folded and assembled in the correct confirmation and that the precursor proteins are not capable to elicit a protective immune response. It has been demonstrated that the precursor proteins are sensitive to protease treatment and can be removed, whereas the virus capsid proteins VP1, VP2 and VP3 are not affected by the protease.

Therefore, the first purification step in the manufacture process of an HAV vaccine is highly efficient in respect to removal of VERO cell proteins and immature precursor proteins.

B. HAV Antigen Content

A competitive EIA is performed with a Test kit E12 (Mediagnost, Tubingen, Germany) according to the manufacturers instructions.

Each sample is serially diluted in dilution buffer and 100 $\mu$l of each sample is tested. The antigen concentration is determined by four parameter analysis using a statistical calculation program (Softmax®, Molecular Devices)

C. Determination of the Total Protein Concentration

The determination of the total protein content is performed by a commercial available bicinchoninic acid (BCA) assay (Pierce) in comparison to a standard protein preparation. 2 ml of a BCA solution are added to 100 $\mu$l of each sample and incubated for 30 min. at 60° C. Subsequently, the optical density of the samples are measured with a photometer at a wavelength of 562 nm. The protein concentration is calculated using a standard curve.

D. Determination of Tissue Culture Infectious Dose ($TCID_{50}$) of purified HAV The determination of $TCID_{50}$ is performed on FRhK-4 cells by serial 1 log dilutions of the samples prepared in cell culture medium. 100 $\mu$l of each serial dilution are added eight times in parallel to FRhK-4 cells grown on microtiter plates.

The cut-off value is calculated as the mean optical density of the negative control wells. All positions with an optical density two times higher than the cut-off value are considered positive. The determination of the $TCID_{50}$ is performed by the maximum likelihood method according to the Poission distribution and expressed as log 10 $TCID_{50}$.

E. Determination of VERO Cell DNA Concentration using PCR

The amount of VERO cell DNA is determined by quantitative PCR as described in U.S. Pat. No. 5,858,658.

As shown in Table 1 the infectivity of the virus (measured by $TCID_{50}$) is not influenced by the purification procedure, whereas the amount of HAV antigen decreased by approximately 50% from 485,000 IU to 263,940 in run 1 and 490,00 IU to 216,558 in run 2. The amount of total protein is reduced from 26,670 mg to 37 mg in run 1 and from 26,100 to 42 mg in run 2. The amount of VERO cell DNA is reduced by a factor of approximately 9,000 by simple filtering method. After enzyme treatment and diafiltration, 2.97 $\mu$g and 6.36 $\mu$g of VERO cell DNA is detected in the diaretentates. On the assumption that 20 IU correspond to one vaccine antigen doses, the amount of VERO cell DNA per vaccine dose after the initial purification by filtration is calculated to be 590 pg and 230 pg, respectively.

TABLE 1

Determination of Efficacy of Purification of HAV

| Sampling | Volume in ml | $TCID_{50}$ in log 10 | HAV antigen in IU | Total protein in mg | VERO cell DNA in $\mu$g | |
|---|---|---|---|---|---|---|
| HAV Concentrate | 10,000 | 10.66 | 485,000 | 26,670 | n.d. | |
| Ultra/diaretenate | 1,050 | 10.63 | 287,700 | 2,263 | 6,380 | RUN 1 |

TABLE 1-continued Determination of Efficacy of Purification of HAV

| Sampling | Volume in ml | TCID$_{50}$ in log 10 | HAV antigen in IU | Total protein in mg | VERO cell DNA in µg | |
|---|---|---|---|---|---|---|
| Diaretentate after enzyme treatment | 1,060 | 10.63 | 263,940 | 37 | 2.97 | |
| HAV Concentrate | 10,000 | 10.09 | 490,000 | 26,100 | 59,000 | |
| Ultra/diaretenate | 1,080 | 10.89 | 225,504 | 1,285 | 8,140 | RUN 2 |
| Diaretentate after enzyme treatment | 1,060 | 10.48 | 216,558 | 42 | 6.36 | |

In addition, the grade of purity of different intermediates of the purification process is calculated by the amount of HAV antigen in relation to total protein. As shown in Table 2 the grade of purity increased from 18.2 IU/mg to 7, 134 IU/mg respectively from 18.8 IU/mg to 5,156 IU/mg.

TABLE 2

Evaluation of grade of purity of intermediates of filtering process

| Intermediates | HAV antigen/total protein in IU/mg - - - Run 1 | HAV antigen/total protein in IU/mg - - - Run 2 |
|---|---|---|
| HAV Concentrate | 18.2 | 18.8 |
| Ultra/diaretentate | 127 | 175 |
| Diaretentate after enzyme treatment | 7,134 | 5,156 |

The filtering process before inactivation of infectious HAV particles has been found to be consistent and highly effective in the reduction of host cell contaminants. The grade of purity increased by a factor of approximately 300, whereas the VERO cell DNA is reduced by a factor of approximately 9000. The loss of HAV antigen, but not of infectivity during the purification process is most probably due to removal of virus specific precursor proteins like protomers and pentamers.

Therefore, the first purification step used in the manufacture of an inactivated HAV vaccine is highly efficient in respect to the removal of host cell contaminants like VERO cell protein and DNA, and immature HAV precursor polypeptides.

EXAMPLE 4

Inactivation of Purified HAV and Isolation of Inactivated HAV Particles

The purified infectious Hepatitis A virus preparation of Example 3 is subjected to inactivation by incubation with 0.1% formalin at 37° C. for 120 hours.

The inactivated HAV preparation is then subjected to gradient centrifugation on a 0–65% sucrose gradient in PBS buffer pH 7.3. After zonal centrifugation different fractions (fraction 11 to 16) as well as the pooled peak fractions (fraction 12 to 14) of the 0–65% sucrose gradient are investigated by Western blot analysis.

A. Characterization of the Purified HAV by Anti-HAV Antibodies

Figure 2A:
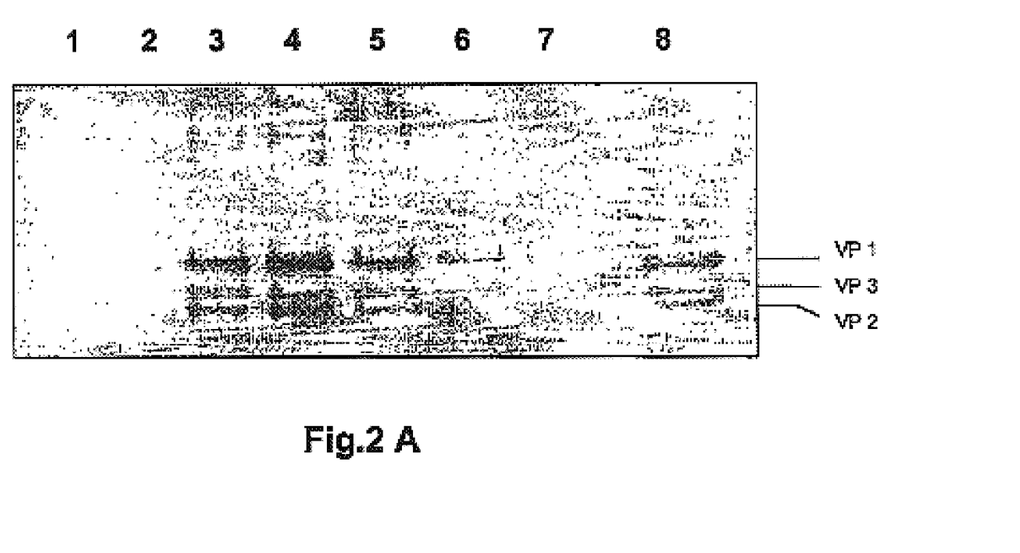
FIG. 2A shows Western blot analysis of different fractions of sucrose-gradient purification of HAV preparation using guinea pig sera raised against capsid proteins.
Figure 2B:
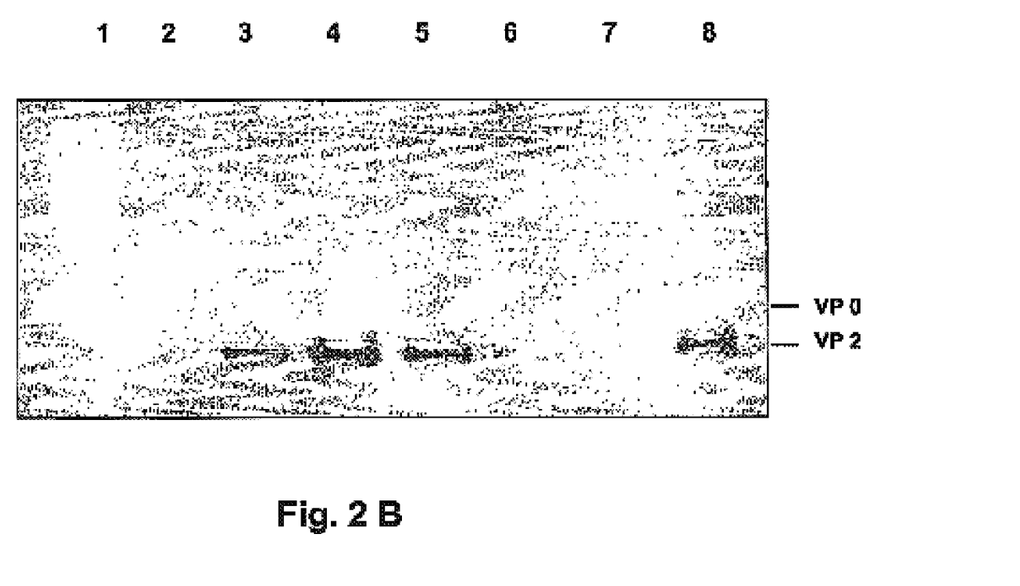
FIG. 2B shows Western blot analysis of different fractions of sucrose-gradient purification of HAV preparation using anti-VP0 specific guinea pig serum. Lane 1: molecular weight standard; lane 2: fraction 11, lane 3: fraction 12, lane 4: fraction 13; lane 5: fraction 14; lane 6: fraction 15; lane 7: fraction 16; lane 8: pool fractions 12–14.

Each fraction is analyzed for HAV antigen by Western blot analysis by incubation with specific polyclonal guinea pig anti-HAV capsid antibodies (FIG. 2A) or a polyclonal guinea pig anti-VP0 antibody (FIG. 2B).

The protein pattern of the purified HAV particles of single fractions 11 to 16 (FIG. 2A and B, lane 2–7) and pooled fractions 12 to 14 (FIGS. 2A and B, lane 8) are shown. The virus capsid proteins VP1, VP2 and VP3 are detected in fractions 12–14 (FIG. 2A, lane 3–5 and 8). Western blot analysis of the respective fractions using antiserum specific to VP0 revealed that VP0 precursor protein is absent and only the capsid protein VP2 is present in the purified preparation (FIG. 2B, lane 3–5 and 8). The purified fractions therefore contained only the mature HAV virions obtained from the supernatant of the cell culture.

B. Characterization of Purified HAV by Anti-VERO Antibodies

Figure 3:
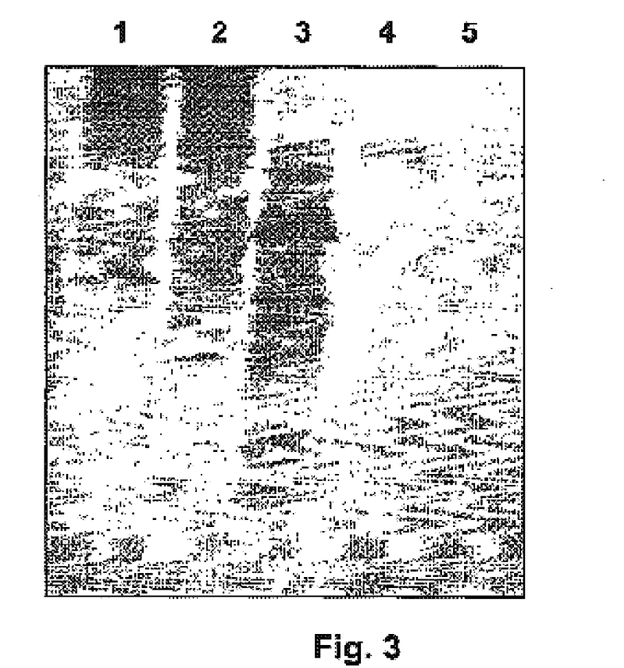
FIG. 3 shows Western blot analysis of different intermediates of the purification process using VERO cell specific antiserum. Lane 1: cell culture supernatant harvest; lane 2: diaretentate 1 (after ultra/diafiltration); lane 3: diaretentate 1 plus protease (after 24 hours of treatment); lane 4: diaretentate 2 (after diafiltration with buffer); lane 5: fraction 12–14 of sucrose-gradient.

Samples of virus harvest and after each purification step are analyzed for HAV antigen by Western blot analysis by incubation with specific polyclonal goat anti-VERO cell protein antibody (FIG. 3).

The analysis of the intermediates of initial filtering process by Western blot analysis clearly demonstrates the efficacy of the purification procedure. FIG. 3 shows the protein pattern of samples of intermediates after Western blot analysis using antiserum raised against VERO cell proteins. A broad range of polypeptides could be detected in the starting material and first intermediates of the purification procedure (FIG. 3, lane 1–3), whereas only slight protein band is left after protease treatment and diafiltration (FIG. 3, lane 4). After final purification by e.g. 0–65% sucrose gradient no VERO cell specific proteins are detectable (FIG. 3, lane 5).

The purification procedure is demonstrated to be highly effective in removing VERO cell contaminants. High molecular weight proteins are fragmented by protease treatment and are removed by the following diafiltration step in the initial purification by filtering. Residual contaminants derived from the nucleic acid degrading agent and the protease treatment as well as of the inactivation process are efficiently removed by final purification step.

C. Characterization of Purified HAV by PCR of VERO Cell DNA

The purified mature HAV particle preparation of pool fractions 12 to 14 is analyzed for contaminating nucleic acid derived from the VERO cell culture as described in U.S. Pat. No. 5,858,658. Calculation of VERO nucleic acids revealed less than 40 pg VERO nucleic acid/100 IU HAV antigen. Therefore, an antigen dose having 20 IU HAV antigen per dose will have less than 8 pg VERO cell nucleic acid.

EXAMPLE 5

HAV Vaccine of Purified Mature HAV Particle

Purified, inactivated mature HAV virion particle preparation is formulated with a phosphate buffered saline (PBS pH7.3) and adjuvanted with different concentrations of an adjuvant. As an examplatory adjuvant aluminum hydroxide is used. Aluminum hydroxide is added to a final concentration of 0,05%, 01% and 0,2% (w/v) to the purified preparation. The preparations are tested for adsorption of the antigen to the adjuvant. The test substances are serially diluted without changing the adjuvant concentration. Test groups of 10 mice each are injected subcutaneously with 0.5 ml of the preparation and four weeks after immunization the animals are analyzed for seroconversion ($ED_{50}$: Effective Dose), antibody titer and neutralizing activity. The results are shown in Tables 3 and 4.

Table 3 shows the seroconversion rates and $ED_{50}$ values of the antigen preparation at different adjuvant concentrations. It is surprisingly found that lower concentrations of adjuvant (0.05%) in the composition are advantageous to induce a higher seroconversion than with a higher concentration of adjuvant (0.2%). Therefore, with the purified preparation of the invention of mature HAV particle less viral antigen is necessary to seroconvert 50% of the animals in the presence of low concentrations of adjuvant.

TABLE 3

Seroconversion rates and $ED_{50}$ values of mice immunized with different concentration of HAV antigen and adjuvant concentrations

| | Al(OH)3 concentration | | |
|---|---|---|---|
| | 0.05% | 0.1% | 0.2% |
| $ED_{50}$ HAV antigen in IU/ml | 0.55 | 0.73 | 1.06 |

TABLE 4

Antibody titre and neutralizing antibody titers of mice immunized with different concentration of HAV antigen and adjuvant concentrations

| | HAV antigen | Al(OH)3 concentration | | |
|---|---|---|---|---|
| | IU/ml | 0.05% | 0.1% | 0.2% |
| Antibody titre mIU/ml | 15 | 6750 | 5970 | 4260 |
| Neutralizing antibody titre activity/ml | 15 | >3247 | 2979 | >3247 |

The results given in Table 4 show that same the antigen concentrations in the immunogenic preparations induce different antibody titers dependent on the adjuvant concentration. At lower adjuvant concentration the antibody titers are higher than at higher adjuvant concentration. The neutralizing antibody titers induced are comparable at same HAV antigen concentrations and different concentrations of the adjuvant. Therefore, the immunogenic composition of the invention comprising a purified preparation of mature HAV particles showed increased immunogenicity at low concentrations of adjuvant. Comparative Immunization studies of HAV vaccine with low adjuvant (0.05%) and without any adjuvant are performed in guinea pigs Table 5.

TABLE 5

Immunization of animals with HAV vaccine with and without adjuvant

| | | Anti-HAV-antibody titers (mIU/ml) | | |
|---|---|---|---|---|
| HAV antigen IU/dose | Adjuvent | After 1. Injection 28 days | After 2. Injection 56 days | After 3. injection 84 days |
| 40 IU | +Alu | 1.330 | 24.183 | 54.086 |
| | −Alu | 336 | 16.376 | 67.306 |

TABLE 5-continued

Immunization of animals with HAV vaccine with and without adjuvant

| | | Anti-HAV-antibody titers (mIU/ml) | | |
|---|---|---|---|---|
| HAV antigen IU/dose | Adjuvent | After 1. Injection 28 days | After 2. Injection 56 days | After 3. injection 84 days |
| 20 IU | +Alu | 624 | 7.921 | 32.706 |
| | −Alu | 1.073 | 4.562 | 33.305 |
| 10 IU | +Alu | <100 | 1.769 | 19.155 |
| | −Alu | 344 | 3.720 | 11.564 |

The results of the experiments given in Tables 3–5 show that the antigen and the adjuvant concentration in an effective vaccine dose can be dramatically reduced to induce a protective immune response against HAV infection. Even more, the immunogenicity and efficacy of the vaccine without any adjuvant is comparable to one comprising a low adjuvant concentration.

EXAMPLE 6

Comparison of HAV Vaccine of Invention with Two Licensed Vaccines

A. Comparison of Immunogenicity

The vaccine of the present invention comprising a purified preparation of mature HAV virion particles with an HAV antigen content of 15–20 IU and a final concentration of 0.05% $Al(OH)_3$ is compared in regard to its immunogenicity with two licensed and commercial available vaccines, VAQTA® 50U (MERCK) and HAVRIX® 1440 (Smithkline Beecham). The vaccines are serially diluted without changing the aluminum concentration. Test groups of mice are immunized s.c. with 0.5 ml of the different vaccine preparations. The sera of each group is pooled and antibody titer and neutralizing antibodies are determined as described in Example 5.

Table 6 shows the induction of antibody titers and neutralizing antibody titres with the different vaccines. Higher antibody titers are elicited when the undiluted vaccine of the present invention is used. The antibody titers of the pooled sera are 3541 mIU/ml with the vaccine of the invention having 15–20 IU/ml. The undiluted licensed vaccine VAQTA® and HAVRIX® are capable to induce 2541 mIU/ml and 691 mIU/ml, respectively. The analysis of neutralizing activity of the pooled sera demonstrate higher neutralizing antibody titers induced with the vaccine of the invention.

TABLE 6

Comparative data of antibody titers and neutralizing antibody titres of different vaccines

| | Vaccine of invention 15–20 IU | VAQTA 50 U | HAVRIX 1440 EU |
|---|---|---|---|
| Antibody titre (mIU/ml) | 3541 | 2541 | 691 |
| Neutralizing antibody titre (activity/ml) | 1520 | 1140 | 349 |

Even though the antigen content of different commercial available vaccine are not standardized and each manufacture has its own test system, the immunogenicity of the candidate vaccine and the commercial available vaccines can be compared by immunization experiments and induction of an effective immune response by seroconversion and antibody titers. The analysis of comparative data demonstrate that a concentration of 15–20 IU of the purified preparation of mature HAV particles of the invention and low concentration of adjuvant (or no adjuvant) is capable to induce an effective immune response against HAV.

B. Comparison of HAV Particles in Vaccine

The HAV preparation of the present invention is compared to two licensed vaccines VAQTA® and HAVRIX® by Western blot analysis with a mixture of monoclonal antibodies of anti-VPO, anti-VP1 and anti-VP3 antibodies.

Figure 4:
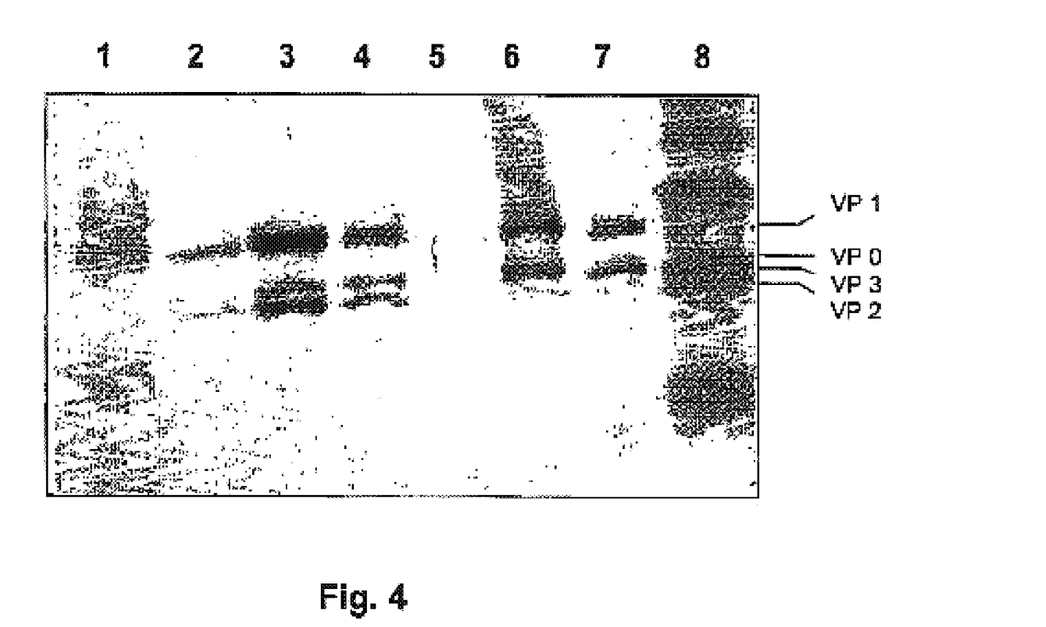
FIG. 4 shows Western blot analysis of HAV preparation consisting of mature HAV particles of the invention and two licensed vaccines using a mixture of anti-VP0, anti-VP1 and anti-VP3 antibodies. Lane 1: molecular weight standard; lane 2: supernatant harvest concentrate 10-fold (prior ultracentrifugation); lane 3: peak fraction 1 of sucrose-gradient; lane 4: peak fraction 2 of sucrose-gradient; lane 5: VERO cell lysate; lane 6: VAQTA 10-fold; lane 7: HAVRIX 10-fold; lane 8: molecular weight standard.

As shown in FIG. 4, the preparation of the present invention is composed of mature HAV particles only, due to the detection of VP2, which derives from the precursor polypeptide VPO by proteolytic cleavage and which is part of the mature virus particle, while VPO is present in provirions and defective virus particles only. The commercial available vaccines comprise also provirions and preprovirions, however in larger amounts than the mature particle. This observation is confirmed by the findings of Armstrong et al. (1993. J. Hepatol. 8:20–26) that VAQTA® HAV vaccine contains both empty provirions and full mature particles in a ratio 3:1.

EXAMPLE 7

Purification of *Streptomyces Griseus* Trypsin from Pronase:

A. Ion Exchange Chromatography 30 g of Pronase (Boehringer Ingelheim) is dissolved in Buffer A (0.02 pyridin, pH 5.0) to a final concentration of 40 mg/ml Pronase. 25 ml of the solution is subjected to cation exchange chromatography on CM Sepharose Cl 6B (Pharmacia) equilibrated with buffer A). The elution is performed at room temperature using a linear gradient with buffer A (0.02 M pryridin) and buffer B (0.75M pyridin pH 5.0) with 5 times the column volume.

Collected fractions are tested for inhibiting properties by mixing samples of the fractions with soy bean inhibitor in a 1:10 ratio (e.g. 1 mg soy bean inhibitor/100 µg protein) followed by a chromatographic substrate assay using S2222. The results are expressed as Δ absorbance units per minute (Δ A/min). The fraction having the highest inhibiting activity to soy bean inhibitor is further analysed by SDS-PAGE and stained with Coomassie.

The trypsin activity is measured by chromogenic assay using N-benzoyl-L-arginine ethyl ester (BAEE, in Tris buffer pH 8.0, 20 mM $CaCl_2$, 25° C.) as substrate and A absorbance units per minute is determined. As a control reference, porcine trypsin solution (1 mg/ml) with a specific activity of $13 \times 10^3$ U/mg is used. The specific activity is defined as the units of trypsin enzyme activity per mg protein. The results are summarized in Table 7.

The chymotrypsin activity is measured by chromogenic assay using 3-carboxymethoxypropionyl-L-arginyl-L-propyl-L-tyrosine-p-notroaniline hydrochloride (S-2586, Chromogenix). The results are expressed Δ absorbance units per minute (Δ A/min).

TABLE 7

Purification of Pronase by ion exchange chromatography

| *Streptomyces griseus* Pronase | Pronase unpurified | Purified fraction |
| --- | --- | --- |
| Protein (g) | 1 | 0.08 |
| Specific activity U/mg | $1.6 \times 10^3$ | $16.5 \times 10^3$ |
| Recovery U in % | 100 | 70 |
| Stability by SDS-PAGE | n.d. | Unstable, low molecular weight fragmentation |
| Inhibition by soy bean inhibitor (% inhibition) | n.d. | 90 ± 0.1 |

TABLE 7-continued

Purification of Pronase by ion exchange chromatography

| *Streptomyces griseus* Pronase | Pronase unpurified | Purified fraction |
| --- | --- | --- |
| Chymotryspin activity (ΔA/min) | 450 | 38 |

*n.d. not determined

Table 7 shows that the fractions containing a protein having trypsin-like activity, as determined by inhibition test with soy bean inhibitor, can be purified by ion exchange chromatography with a specific activity which is about 10 times higher than of Pronase and with a recovery of about 70%. However, the protein is unstable and shows not a single band, but various bands in SDS-PAGE. This is indicative of fragmentation and autocleavage of the protein.

B. Affinity Chromatography on Immobilized Benzamidine

A Benzamidine Sepharose 6B fast flow (Pharmacia) column equilibrated with buffer A (50 mM Tris, 0.5 M NaCl pH 7.0) is loaded with 40 ml of a Pronase solution (75 mg/ml, buffer A). Elution is performed with Buffer B (50 mM Tris, 0.5 M NaCl pH 7.0, 10 mM benzamidine hydrochlorid pH 7.0), buffer C (0.5 M NaCl, 0.6 M arginine, pH 5.5) or buffer D (0.5 M NaCl, 1 M arginine, pH 5.5).

The fractions collected are tested for inhibiting properties using soy bean inhibitor, as well as trypsin and chymotrypsin activity as described in Example 7A. The specific activity is determined as units of enzyme activity per mg protein.

TABLE 8

Purification of Pronase by affinity chromatography on immobilized benzamidine and elution with benzamidine
Affinity chromatography and elution with benzamidine (Buffer B)

| *Strepromyces griseus* pronase | Pronase unpurified | Purified fraction |
| --- | --- | --- |
| Protein (g) | 3 | 0.13 |
| Specific activity U/mg | $1.6 \times 10^3$ | $19 \times 10^3$ |
| Recovery U in % | 100 | 60 |
| Stability by SDS-PAGE | stable | stable |
| Inhibition by soy bean inhibitor (% inhibition) | n.d. | 99.98 ± 0.1% |
| Chymotryspin activity (ΔA/min) | n.d. | 0.1 |

The results summarized in Table 8 show that by competitive elution with benzamidine, 60% of purified trypsin-like activity of Pronase is recovered with a specific activity of about 140 U/µg protein. However, the purified trypsin-like protease containing fraction is preferably further purified and the benzaminide removed prior to use in processes which involve cell culture growth or production of biologicals for application in humans.

TABLE 9

Purification of Pronase by affinity chromatography on immobilized benzamidine and elution with 0.6 M arginine and 1 M arginine

| *Streptomyces griseus* Pronase | Pronase unpurified | Purified fraction |
| --- | --- | --- |
| Affinity chromatography and elution with 0.6 M arginine (Buffer C) | | |
| Protein (g) | 3 | 0.13 |
| Specific activity U/mg | $1.6 \times 10^3$ | $26 \times 10^3$ |
| Recovery U in % | n.d. | 63 |
| Stability by SDS-PAGE | stable | stable |

TABLE 9-continued

Purification of Pronase by affinity chromatography on immobilized benzamidine and elution with 0.6 M arginine and 1 M arginine

| Streptomyces griseus Pronase | Pronase unpurified | Purified fraction |
|---|---|---|
| Inhibition by soy bean inhibitor (% inhibition) | n.d. | 99.89 ± 0.1% |
| Chymotrypsin activity (ΔA/min) | n.d. | <0.1 |
| Affinity chromatography and elution with 1 M arginine (Buffer D) | | |
| Protein (g) | 3 | 0.13 |
| Specific activity U/mg | $1.6 \times 10^3$ | $46.5 \times 10^3$ |
| Recovery U in % | n.d. | 71% |
| Stability by SDS-PAGE | stable | stable |
| Inhibition by soy bean inhibitor (% inhibition) | n.d. | 99.99 ± 0.1% |
| Chymotrypsin activity (ΔA/min) | n.d. | <0.1 |
| LAL (EU/1000 U) | 88 | <4 |

As can be seen from results in Table 9, about 63% of the initial trypsin-like activity of Pronase is recovered when using a buffer comprising 0.6 M arginine, whereas about 71% is recovered with a buffer comprising 1M arginine. The purified SGT eluted with arginine from a benzamidine affinity carrier also had a higher specific activity compared to SGT obtained by ion exchange chromatography or elution with benzamidine from a benzamidine carrier. Further, a product of higher purity and specific activity is obtained when a buffer comprising increasing molarity of arginine is used.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of producing complete Hepatitis A Virus (HAV) particles comprising the steps of providing a cell culture supernatant of an HAV infected VERO cell culture; concentrating said concentrated cell culture supernatant; treating an HAV preparation from the cell culture supernatant of the HAV infected cell culture with a nucleic acid degrading agent and a protease; diafiltering to remove impurities to obtain a purified preparation of complete HAV particles in a single step.

2. The method of claim 1, wherein the nucleic acid degrading agent is an enzyme.

3. The method according to claim 1, wherein said protease is Pronase or an enzymatically active fraction thereof.

4. The method according to claim 1, wherein said protease is purified Streptomyces griseus trypsin.

5. The method according to claim 1, wherein said cells are grown in a serum free or serum and protein free medium.

6. The method according to claim 1, wherein said purified preparation of complete HAV particles has at least about 5000 IU of HAV antigen/mg protein.

7. The method according to claim 1, further comprising a step of treating the preparation of complete HAV particles with a virus inactivating agent.

* * * * *